United States Patent [19]

Chrisman et al.

[11] Patent Number: 4,672,218

[45] Date of Patent: Jun. 9, 1987

[54] METHOD FOR DETERMINING THE ONSET OF CRYSTALLIZATION

[75] Inventors: Ray W. Chrisman; Richard D. McLachlan; Richard S. Harner, all of Midland, Mich.

[73] Assignee: The Dow Chemical Company, Midland, Mich.

[21] Appl. No.: 678,114

[22] Filed: Dec. 4, 1984

[51] Int. Cl.⁴ ............................................. G01N 21/49
[52] U.S. Cl. .................................. 250/574; 250/222.2
[58] Field of Search ............ 250/573, 574, 576, 222.2, 250/227; 356/441

[56] References Cited

U.S. PATENT DOCUMENTS 3,695,763  10/1972  Shiuh .................................. 356/441

Primary Examiner—Gene Wan
Attorney, Agent, or Firm—Learman and McCulloch

[57] ABSTRACT

A method for determining the onset of nucleation wherein a zone of a translucent fluid in which crystals may be formed is illuminated by a beam of light. When crystallization commences the crystals in the illuminated zone reflect and scatter light. Some of the scattered light is collected and transmitted to a light sensitive detector operable to generate a signal indicative of nucleation. Upon detection of nucleation either manual or automatic procedures may be instituted to modify the crystallization process in an appropriate manner.

23 Claims, 2 Drawing Figures

METHOD FOR DETERMINING THE ONSET OF CRYSTALLIZATION

This invention relates to a method for determining the onset of crystallization in a fluid medium wherein the refractive indices of the crystalline material and the fluid medium are different.

BACKGROUND OF THE INVENTION

The manufacture of crystalline products is effected by a number of known processes in which crystals are formed in a fluid medium commonly referred to as the mother liquor. In one known process, the mother liquor, which is initially at a relatively high temperature, is cooled rapidly until crystallization commences, at which time the cooling rate is reduced or stopped, to allow the crystals to grow at a slow, controlled rate. Failure to reduce the cooling rate at the appropriate time often results in the formation of very large numbers of small, impure crystals which are unsatisfactory and must be purified by repetition of the crystallization process.

Other crystallization processes are controlled by distilling part of the solvent from the solution at an essentially constant temperature. At the onset of crystallization, the rate of solvent removal is reduced or interrupted by reducing the heat input or by returning all or part of the condensed solvent to the crystallizer.

In some crystallization processes the crystalline products are crystallized simultaneously with the reaction in which the product is formed. This typically is accomplished by dissolving one reactant in a solvent in which the product has limited solubility. The second reactant (either in pure form or dissolved in the same solvent) is then caused to flow into the vessel containing the solution of the first reactant. At the onset of crystallization it is necessary to stop or slow the flow of the second reactant.

In all of the processes referred to above optimum production of the crystalline product depends in large part on the detection of the time at which nucleation commences so that the process under way can be appropriately modified. Heretofore the approximate commencement of nucleation has been determined by the inefficient and labor intensive method of visually monitoring the liquor in its vessel, or by the use of one of two instrumental methods.

One of the instrumental methods is dependent on the detection of an exotherm accompanying the crystallization and was found to be impractical when dealing with commercial scale production of the product. The second instrumental method was based on the determination of differences of refractive indices and also proved to be ineffective in terms of both sensitivity and durability.

The method according to the invention relies upon the detection of light scattered by the presence of crystals in a fluid medium having a refractive index different from that of the crystals.

The same principles upon which the method is based are applicable to the detection of substances other than crystals. Thus the method has utility in a variety of applications.

SUMMARY OF THE INVENTION

A method according to the invention for determining the presence in a fluid medium of crystals or other substances having a refractive index different from that of the fluid medium comprises introducing a beam of light into a transparent or translucent fluid medium to illuminate a zone thereof. The fluid medium then is treated to cause the substance that is to be detected to enter the illuminated zone. As long as there is no such substance in the illuminated zone, the light is relatively undisturbed. When the substance enters the illuminated zone, however, the substance scatters or reflects the light in all directions. The scattering of the light may be detected, thus indicating the presence of the substance in the fluid medium.

The method according to the invention is particularly useful in detecting the onset of nucleation in the manufacture of a crystalline product. In the production of such a product use is made of a transparent or translucent liquid medium containing ingredients from which crystals may be formed following the treatment of the fluid medium in a prescribed manner. Upon nucleation, crystals present in the illuminated zone will reflect and scatter the light in such zone. Some of the scattered light may be collected and transmitted to a light sensitive sensor or detector which is operable to indicate the formation of crystals. By monitoring the intensity of the scattered light, and variations in its intensity, it is possible not only to detect the onset of crystallization, but also to effect modifications of the process, either manually or automatically, so as to result in the production of crystals of the desired size in the optimum time period.

The illuminating light may be introduced into the liquid medium by means of a first set of one or more optical fibers and the scattered light may be collected by means of a second set of one or more optical fibers. The sets of fibers may be mounted in a single fiber optic probe in which the illuminating and light collecting fibers are so oriented that the latter are located in a position to receive light reflected or scattered by particles illuminated by the illuminating fibers. Examples of suitable fiber optic probes, among others, are described in a commonly owned copending application titled Fiber Optic Probe.

Scattered light collected by the probe may be transmitted via the collecting fibers to a light sensitive detector operable to generate an electrical signal. The signal may activate a bell, light, recorder, or other device to alert a person who then may take appropriate action to modify the process, or the signal may be used to actuate a valve or switch which results in process modification.

It is preferred to stir, agitate, or otherwise set in motion the fluid containing the substance that is to be detected in such manner as to ensure that the substance, if present in the fluid, traverses the illuminated zone.

THE DRAWINGS

FIG. 1 is a diagrammatic view of apparatus which may be used in practicing the method; and FIG. 2 is a graph illustrative of signals produced by scattered light over a period of time and indicating the onset of nucleation and the growth of crystals.

DETAILED DESCRIPTION

Figure 1:
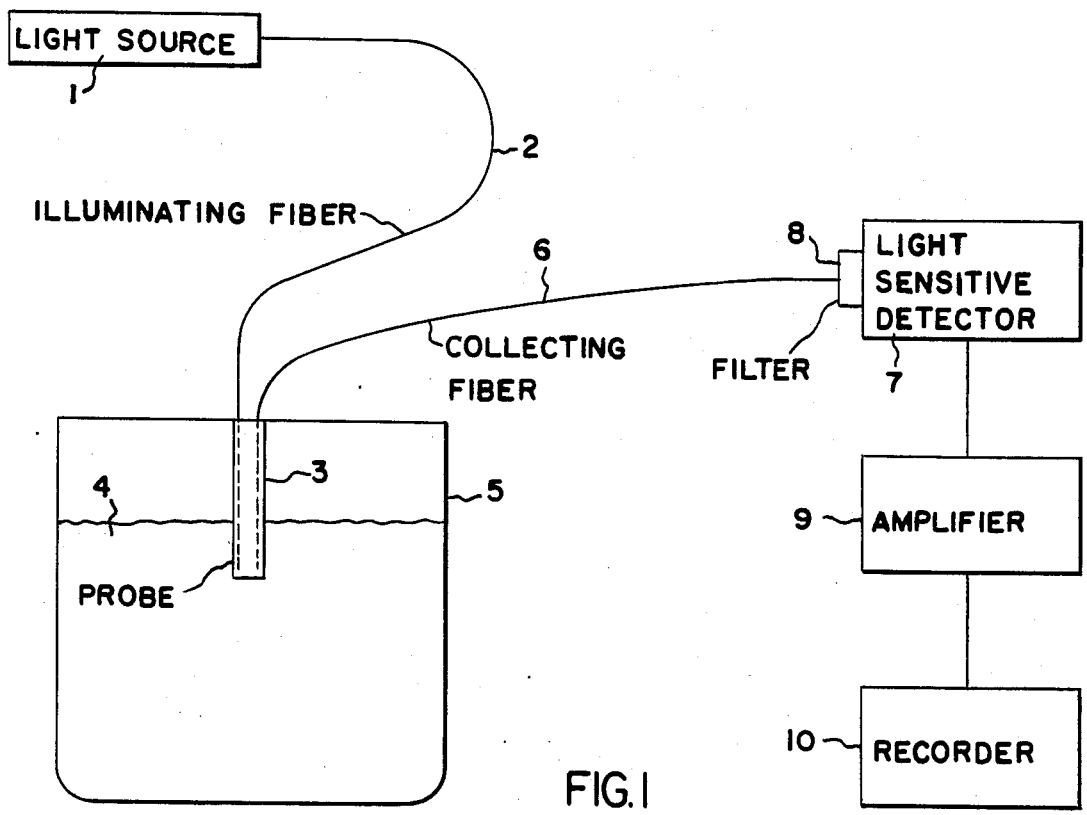

Apparatus for use in practicing the method according to the invention is disclosed in FIG. 1 as comprising a light source 1 coupled to one end of an illuminating optical fiber 2, the opposite end of which is fitted into a probe 3 formed of suitable material enabling it to be immersed in a transparent or translucent liquid medium 4 in a tank or other appropriate vessel 5. The medium 4 sometimes will be referred to herein as a continuous fluid phase.

The probe 3 also houses one end of a light collecting and transmitting optical fiber 6 which extends from the probe toward a light sensitive detector 7 that is operable to generate an electrical signal in response to energization by light. Interposed between the fiber 6 and the detector 7 may be an optical filter 8 which limits the light passing therethrough to a selected wavelength. The detector 7 is coupled to an amplifier 9 which, in turn, is coupled to a strip chart recorder 10 or any other suitable device, such as a process control valve, switch, or computer.

The illuminating fibers and the collecting fibers are so arranged in the probe 3 that the longitudinal axes at the free ends thereof converge outwardly of the probe and along lines which intersect at a common point on the longitudinal axis of the probe. Thus, a beam of light emitted from the fiber 2 will illuminate a zone of the fluid medium 4. Should the fluid medium contain materials which scatter the light, some of the scattered light will be directed backwardly toward and impinge upon the fiber 6. Such back-scattered light will be collected by the fiber 6 and transmitted thereby to the devices 7–10. The light scattering materials sometimes will be referred to herein as a discontinuous phase.

The light source 1 is maintained in a protected location external of the medium 4 and may be a Math Associates type E1500F light emitting diode which produces a suitable light, such as a monochromatic, near infrared light having a wavelength of 890 nm. The detector 7 may be a United Detector Technology type 6DP silicon photodiode. The filter 8 may be a Corion Corporation model S10-890 bandpass filter, a monochromator, or other filter compatible with the wavelength produced by the light source 1. The amplifier 9 may be a United Detector Technology model 301C transimpedance amplifier and the strip chart recorder 10 may be a Sargent-Welch model SRG-2.

It is not essential that a light emitting diode be used as the light source or that a silicon diode be used as the detector. It is possible to make use of other light sources, such as a laser diode, a continuous wave gas laser, or an incandescent lamp, and a different compatible photodiode, a photomultiplier tube, or other sensitive light detection device as the detector.

When the method is used in connection with the manufacture of a crystalline product, the medium 4 in the vessel 5 may be a liquid that is stirred, agitated, or otherwise set in motion, as is common, by conventional means, brought to and maintained at a prescribed temperature, and otherwise treated in such manner as is appropriate and conventional to effect crystallization. Practice of the method according to the invention does not require any changes to be made in the conventional crystallization processes for the production of specific products.

Prior to the formation of any crystals in the medium 4, the probe is so located with respect to the medium as to cause a beam of light to be introduced from a selected point into such medium to illuminate a zone thereof. The point of introduction may be an opening in the wall of the vessel through which the probe is inserted, or the probe may be immersed in the medium so as to illuminate any desired part thereof. Prior to the commencement of crystallization, relatively little or none of the light introduced into the medium is reflected or back-scattered toward the probe and onto the fiber 6. Upon the onset of nucleation, however, crystalline particles appear in the illuminated zone of the medium 4 and scatter the incident light in all directions.

Some of the light scattered by crystalline particles in the illuminated zone of the vessel 5 will impinge upon the fiber 6 as pulses. Such pulses will be transmitted by the fiber 6 to the apparatus 7–10 that is optically downstream from the probe 3. The intensity of the pulses of scattered light transmitted by the fiber 6 is approximately proportional to the surface area of a crystal which causes the scattering, and the number of such pulses is directly proportional to the number of crystals traversing the illuminated zone.

Pulses of light transmitted by the fiber 6 pass through the filter 8 and into the detector where they are converted into electrical signals which are amplified by the amplifier 9 in such manner as to drive the strip chart recorder 10. The recorder thus is enabled to respond to electrical signals produced by the collected scattered light to record on a strip chart data that are proportional to the intensity of scattered light. By observing the charted data produced by the recorder it is possible for an operator to detect not only the commencement of crystallization, but also to monitor the crystalline growth.

Figure 2:
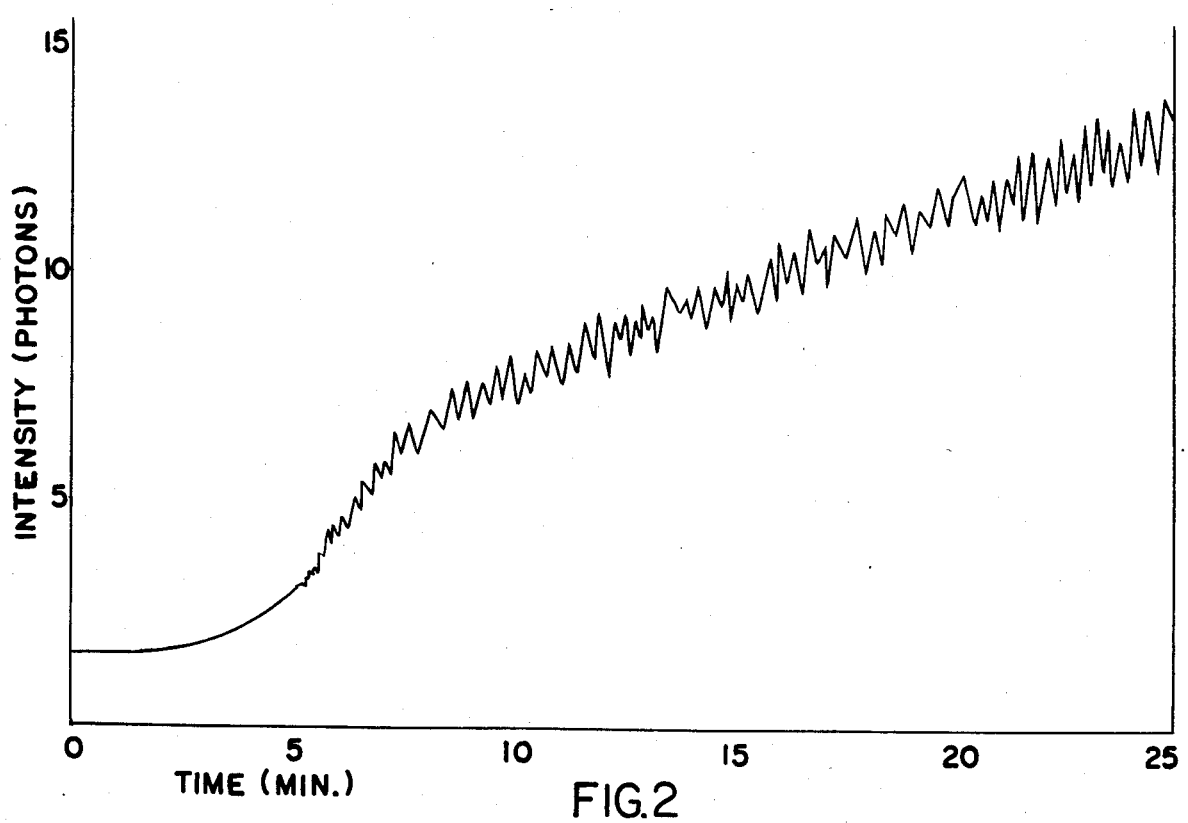

FIG. 2 represents a graph of the kind produced on a strip chart by operation of the recorder 10 and on which are displayed data generated by the scattering of light in the medium 4 as a result of the formation therein of crystals. The graph plots the intensity, in photons for example, of scattered light pulses which impinge on the fiber 6 and are transmitted thereby over a period of time to the recorder 10 via the units 7–9.

At the lower, left hand end of the graph the charted line is relatively flat which indicates a low level, fairly constant value for the light intensity such as is the case when there are few or no light reflecting particles in the medium 4. The charted line soon becomes irregular, however, indicating the impingement on the fiber 6 of light pulses of varying intensities, thereby indicating the presence of crystalline particles in the fluid medium. The graph shows an overall continuing increase in the intensity and frequency of light pulses transmitted by the fiber 6, thereby indicating not only the commencement of nucleation, but also the growth of crystals.

Once the onset of nucleation has been detected, appropriate manual or automatic procedures for modifying the process may be initiated and maintained as has been indicated hereinbefore.

A particular advantage of using a probe of the kind containing both the illuminating and the collecting fibers is that the illuminating light and the collected back-scattered light radiate from and are collected at substantially the same point in the liquid medium. Thus, the onset of nucleation can be detected reliably even in media of such absorbtivity or turbidity that the illuminated zone is relatively shallow.

The method is not limited to the detection of the presence of crystals or other discontinuous phase solid particles in a continuous phase liquid medium. It also may be used to detect the presence of non-crystalline solids in liquid or gaseous media, as well as for the detection of gas bubbles and immiscible liquid droplets in liquid or gaseous media. Thus, the method may be utilized in a wide variety of applications.

What is claimed is:

1. In a chemical process, a method of determining the presence in a translucent, continuous first phase fluid medium contained in a vessel of a discontinuous second phase having a refractive index different from that of said first phase, said method comprising:
(a) inserting a probe in said vessel at such level as to be immersed in said fluid medium;
(b) illuminating via said probe a zone of said fluid medium prior to the time that said second phase is present in said illuminated zone so that the presence of said second phase in said illuminated zone may scatter light;
(c) collecting via said probe light scattered by said second phase present in said illuminated zone; and
(d) transmitting said collected light to a light sensitive detector.

2. The method of claim 1 including treating said fluid medium in response to the detection of said scattered light.

3. The method of claim 1 wherein said second phase comprises crystals and said first phase comprises a liquid.

4. The method of claim 1 wherein said second phase comprises droplets of a first liquid and said first phase comprises a second liquid, said first and second liquids being immiscible.

5. The method of claim 1 wherein said second phase comprises droplets of a liquid and said first phase comprises a gas.

6. The method of claim 1 wherein said second phase comprises a non-crystalline solid and said first phase comprises a liquid.

7. The method of claim 1 wherein said second phase comprises gas bubbles and said first phase comprises a liquid.

8. The method of claim 1 wherein said second phase comprises solid particles and said first phase comprises a gas.

9. The method of claim 1 wherein said zone of said first phase is illuminated by light transmitted from a source thereof to said fluid medium via at least one optical fiber.

10. The method of claim 1 wherein said zone is illuminated by light emanating from a light emitting diode.

11. The method of claim 1 wherein said zone is illuminated by light emanating from a laser diode.

12. The method of claim 1 wherein said zone is illuminated by light emanating from a continuous wave laser.

13. The method of claim 1 wherein said light emanates from an incandescent lamp.

14. The method of claim 1 wherein said detector comprises a photodiode.

15. The method of claim 1 wherein said detector comprises a photomultiplier.

16. The method of claim 1 including filtering the scattered light prior to transmitting it to said detector.

17. In a crystallization process, a method of determining the formation in a translucent fluid medium contained in a vessel of light scattering crystals having a refractive index different from that of said medium, said method comprising:
(a) inserting a probe in said vessel at such level as to be immersed in said fluid medium;
(b) illuminating via said probe a zone of said fluid medium prior to the formation of crystals therein so that the presence of crystals in said illuminated zone may scatter light;
(c) collecting via said probe light scattered by crystals present in said zone; and
(d) transmitting the collected light to light detecting means.

18. The method of claim 17 including treating said liquid medium in a manner to cause crystals therein to traverse said zone.

19. The method of claim 18 including stirring said liquid medium.

20. The method of claim 18 including agitating said liquid medium.

21. The method of claim 18 including setting said liquid medium in motion.

22. The method of claim 17 including illuminating said zone by transmitting light to said probe via at least one optical fiber and transmitting scattered light from said probe via at least one other optical fiber.

23. The method of claim 17 including modifying said fluid medium in response to the detection of said scattered light.

* * * * *